United States Patent
Pawlow et al.

(10) Patent No.: US 8,053,621 B2
(45) Date of Patent: Nov. 8, 2011

(54) SOLVENT TREATMENT METHODS AND POLYMERIZATION PROCESSES EMPLOYING THE TREATMENT METHODS

(75) Inventors: James H. Pawlow, Akron, OH (US); William L. Hergenrother, Akron, OH (US)

(73) Assignee: Bridgestone Corporation, Akron, OH (US)

( * ) Notice: Subject to any disclaimer, the term of this patent is extended or adjusted under 35 U.S.C. 154(b) by 817 days.

(21) Appl. No.: 11/966,612

(22) Filed: Dec. 28, 2007

(65) Prior Publication Data

US 2008/0167509 A1 Jul. 10, 2008

Related U.S. Application Data

(60) Provisional application No. 60/877,832, filed on Dec. 29, 2006.

(51) Int. Cl.
*C07C 7/12* (2006.01)
(52) U.S. Cl. ........ 585/824; 585/820; 585/821; 585/823; 210/660; 210/690
(58) Field of Classification Search .................. 585/856, 585/858, 820, 830, 821, 823, 824; 210/660, 210/690
See application file for complete search history.

(56) References Cited

U.S. PATENT DOCUMENTS

| | | | | |
|---|---|---|---|---|
| 2,856,392 | A * | 10/1958 | Tegge et al. | 526/237 |
| 3,409,691 | A * | 11/1968 | Small | 585/824 |
| 3,922,217 | A * | 11/1975 | Cohen et al. | 208/299 |
| 4,108,916 | A * | 8/1978 | Mears | 585/839 |
| 4,167,531 | A | 9/1979 | Potts | |
| 4,326,046 | A * | 4/1982 | Miyaka et al. | 525/276 |
| 4,433,194 | A * | 2/1984 | Symon et al. | 585/803 |
| 4,461,883 | A * | 7/1984 | Takeuchi et al. | 526/139 |
| 4,504,639 | A * | 3/1985 | Ueno et al. | 526/146 |
| 5,191,149 | A * | 3/1993 | Kulkarni | 585/802 |
| 5,496,940 | A * | 3/1996 | Lawson et al. | 540/450 |
| 5,888,402 | A * | 3/1999 | Hommeltoft et al. | 210/690 |
| 6,596,914 | B2 | 7/2003 | Gore et al. | |
| 2009/0000990 | A1 * | 1/2009 | Toida | 208/219 |

FOREIGN PATENT DOCUMENTS

WO WO 2005073348 A1 * 8/2005
WO WO 2007143041 A2 * 12/2007

OTHER PUBLICATIONS

Armarego, et al., Purification of Laboratory Chemicals, 5th edition, Elsevier, 2003, on-line version available at www.knovel.com.*
Threadingham, et al., "Synthetic Rubber, 3." in Ullmann's Encyclopedia of Industrial Chemistry, Wiley-VCH, available on-line Apr. 30, 2004.*
LeVan, et al., "Adsorption and Ion Exchange" in Perry's Chemical Engineer's Handbook, 7th edition, 1997, McGraw-Hill, available on-line at www.knovel.com.*
Machine Translation of WO 2005073348 A1.*

* cited by examiner

*Primary Examiner* — In Suk Bullock
*Assistant Examiner* — Bradley Etherton
(74) *Attorney, Agent, or Firm* — Meredith E. Hooker; Arthur M. Reginelli

(57) ABSTRACT

A method for treating a hydrocarbon solvent, the method comprising continuously introducing a hydrocarbon solvent to a liquid medium containing hydrogen ions; allowing the hydrocarbon solvent to be in contact with the liquid medium for at least 1 minute; continuously removing hydrocarbon solvent from the liquid medium to provide a treated hydrocarbon solvent stream.

18 Claims, 2 Drawing Sheets

SOLVENT TREATMENT METHODS AND POLYMERIZATION PROCESSES EMPLOYING THE TREATMENT METHODS

This application claims the benefit of U.S. Pat. Application Ser. No. 60/877,832, filed on 29 Dec. 2006, which is incorporated herein by reference.

TECHNICAL FIELD

One or more embodiments of the present invention are directed toward a method for treating an organic solvent; the treated solvent may be advantageous for use in solution polymerization processes particularly those that employ metals that are deleteriously affected by impurities such as those present in organic solvents. In one or more embodiments, the treatment method includes contacting the solvent with a hydrogen ion and/or proton donor such as a mineral acid. In these or other embodiments, the solvent is contacted with a medium containing acidic groups.

BACKGROUND

Many industrial processes employ organic solvents. The organic solvents may include hydrocarbon solvents such as aliphatic and aromatic solvents. The industrial processes may include those that are sensitive to impurities. Inasmuch as may processes employ bulk or technical-grade solvents, the solvent may be a source for a contaminant. Also, many industrial processes reuse or recycle solvents thereby providing another source of impurity to the industrial process.

For example, many polymers are produced by polymerization methods that employ transition metal-containing catalyst. These catalysts are often designed to provide very specific polymeric configurations and characteristics. While these catalyst systems are advantageous in this regard, their ability to perform as desired can be deleteriously impacted by impurities.

While it is common in the art, particularly in the manufacture of olefinic polymerization, to purify solvents using filtration techniques such as carbon adsorption or silica or alumina adsorption, the same has not proven to be entirely satisfactory for some polymerization systems, especially on the industrial scale.

DRAWINGS

SUMMARY

Figure 1:
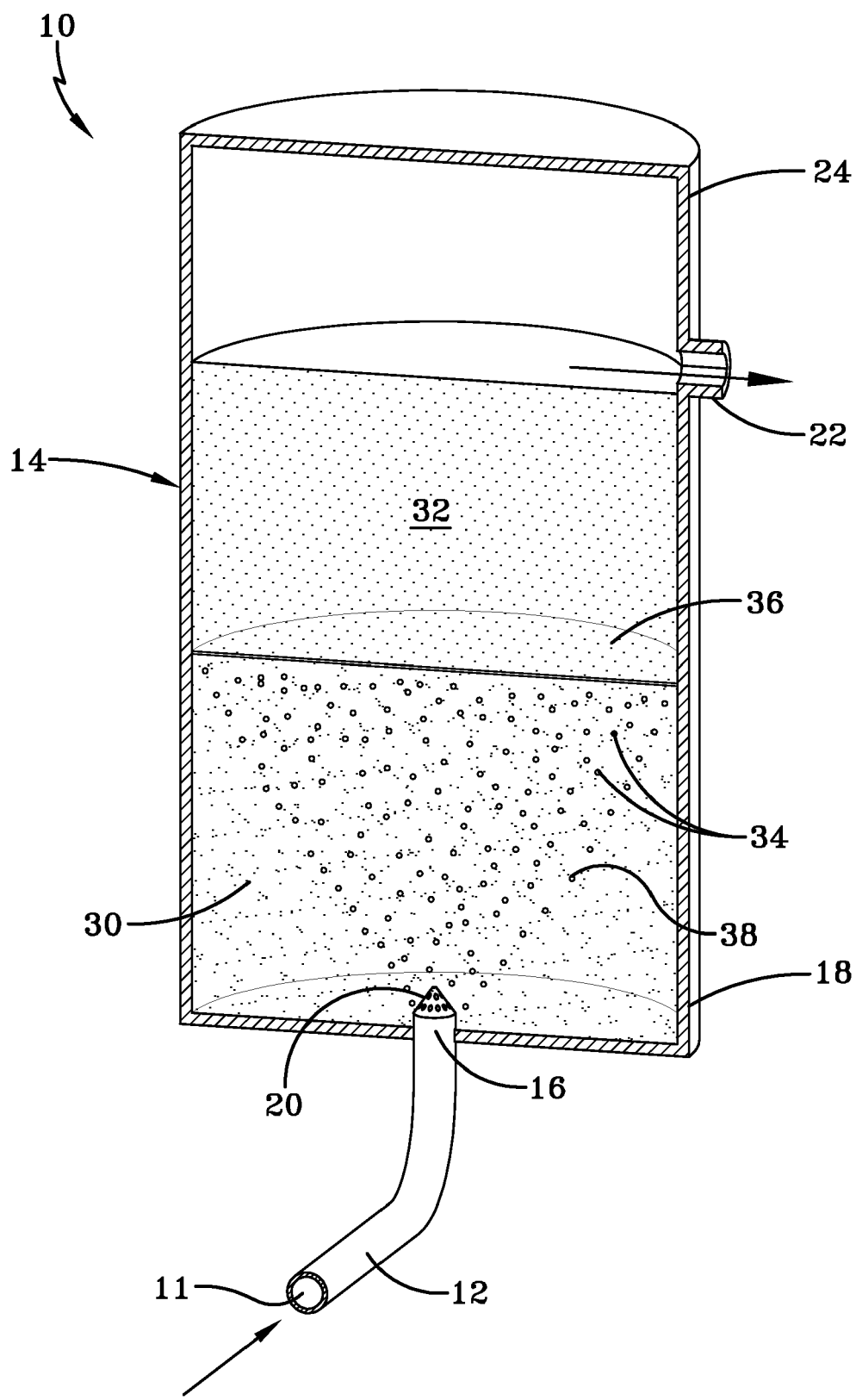
FIG. 1 is a schematic depiction of a treatment process of one embodiment of the present invention where a liquid solution of acid is employed to treat a solvent stream.

A method for treating a hydrocarbon solvent, the method comprising: continuously introducing a hydrocarbon solvent to a liquid medium containing hydrogen ions; allowing the hydrocarbon solvent to be in contact with the liquid medium for at least 1 minute; continuously removing hydrocarbon solvent from the liquid medium to provide a treated hydrocarbon solvent stream.

A method for treating a hydrocarbon solvent, the method comprising: continuously introducing a hydrocarbon solvent to a resinous medium containing one or more proton donor groups; allowing the hydrocarbon solvent to be in contact with the resinous medium for at least 1 minute; continuously removing hydrocarbon solvent from the resinous medium to provide a treated hydrocarbon solvent stream.

DETAILED DESCRIPTION OF ILLUSTRATIVE EMBODIMENTS

One embodiment of the present invention includes treating an organic solvent by contacting the organic solvent with a liquid medium containing a hydrogen ion and/or proton donor. Another embodiment includes contacting an organic solvent with solid medium containing a hydrogen donor moiety. In one or more embodiments, the treatment process is continuous whereby a stream of solvent is continuously treated, and the treated solvent is continuously removed from the treatment process. In one or more embodiments, the treated solvent is employed as a solvent within a solution polymerization process.

The solvents that may be treated by one or more embodiments of the present invention include hydrocarbons. In one or more embodiments, the hydrocarbons are non-reactive with the hydrogen ion or proton source and/or non-reactive with the hydrogen donor moiety. In one or more embodiments, the hydrocarbons are liquid at standard conditions of temperature and pressure. In other embodiments, the hydrocarbons are liquid at the conditions under which treatment according to this invention occurs. In other words, where the process of this invention is operated at elevated pressures, hydrocarbons having lower boiling points (e.g. butane) can be treated according to this invention. The hydrocarbons include both aliphatic and aromatic compounds. Types of aliphatic compounds include cyclic and acyclic compounds. Exemplary cyclic aliphatic compounds include butane, isobutene, cyclopentane, cyclohexane, cycloheptane, cyclooctane, and cyclodecane. Exemplary acyclic aliphatic compounds include n-pentane, iso-pentane, n-hexane, methyl pentane, n-heptane, methyl hexane, ethyl pentane, n-octane, 2-ethyl hexane, n-nonane, and n-decane. Exemplary aromatic compounds include benzene, ethyl benzene, and xylene. In one or more embodiments, the solvent treated is a bulk cut or mixture of hexanes, which includes a distillate fraction of aliphatic $C_6$ hydrocarbons and similar compounds.

In one embodiment, solvent is continuously treated by contacting a stream of solvent with a liquid solution containing one or more hydrogen ions, which may be referred to as an acidic liquid or simply as the liquid medium. The solution containing the one or more hydrogen ions may include a liquid medium including a mineral acid. In one or more embodiments, the solution may include an aqueous solution of one or more mineral acids. Types of useful acids may include monoprotic, diprotic, and triprotic acids. Exemplary monoprotic acids include nitric acid and hydrochloric acid. Exemplary diprotic acids include sulfuric acid. Exemplary triprotic acids include phosphoric acid.

In one or more embodiments, the acids may be characterized by a pKa at standard conditions within water of less than 3.0, in other embodiments less than 2.5, in other embodiments less than 2.0, in other embodiments less than 1.5, in other embodiments less than 1.0, in other embodiments less than 0.5, and in other embodiments less than 0. In these or other embodiments, the acid may be characterized by a pKa (standard conditions within water) of greater than −15, in other embodiments greater than −11, in other embodiments greater than −10, and in other embodiments greater than −9.

The concentration of the acid within the liquid medium may be tailored to desired specifications. Those skilled in the art know or will be able to readily determine the maximum concentration of a given acid. In particular, those skilled in the art appreciate that certain acids may be highly concentrated in a liquid state. For example, fuming sulfuric acid is or is nearly a pure liquid material. For purposes of this specification, however, reference to liquid medium containing hydrogen ions will include reference to liquid acids (e.g. fuming sulfuric acid), as well as highly concentrated acid solutions such as those containing minimal or low percentages of water (e.g. sulfuric acid at about 95% by weight). In one or more embodiments, the concentration of acid within the liquid medium is at least about 30%, in other embodiments at least about 50%, in other embodiments at least about 75%, in other embodiments at least about 90%, in other embodiments at least 95%, and in other embodiments at least about 99% of the maximum concentration that can be achieved and yet obtain a stable solution. In particular embodiments where sulfuric acid is employed, the liquid media may contain at least 80% by weight, in other embodiments at least 85% by weight, in other embodiments at least 90% by weight, and in other embodiments from about 75% to about 95%, or up to about 98% by weight sulfuric acid in liquid solution. In other embodiments, fuming sulfuric acid could be used.

The amount of liquid (which contains hydrogen atoms deriving from the mineral acid) employed compared to the amount of solvent being treated may be expressed in terms of the volume ratio of acidic liquid to solvent. In one or more embodiments, the volume of ratio of liquid to solvent may be at least 1:1, in other embodiments at least 2:1, in other embodiments at least 10:1, in other embodiments at least 20:1, and in other embodiments at least 30:1. In these or other embodiments, the volume ratio of acidic liquid to solvent may be less than 200:1, in other embodiments less than 150:1, in other embodiments less than 100:1, and in other embodiments less than 60:1.

In one or more embodiments, the residence time, which is the amount of time the solvent and acidic liquid are placed in contact with each, be at least 1 minute, in other embodiments at least 3 minutes, in other embodiments at least 5 minutes, and in other embodiments at least 7 minutes. In these or other embodiments, the residence time may be less than 30 minutes, in other embodiments less than 20 minutes, in other embodiments less than 15 minutes, and in other embodiments less than 12 minutes.

The conditions under which the solvent and acidic liquid are contacted may include a temperature of at least 0° C., in other embodiments at least 10° C., and in other embodiments at least 20° C. In these or other embodiments, the temperature may be less than 75° C., in other embodiments less than 50° C., in other embodiments less than 35° C., and in other embodiments less than 30° C. The pressure may range from slight vacuum up to 6 atmospheres, in other embodiments less than 4 atmospheres, and in other embodiments less than 2 atmospheres. In one or more embodiments, the conditions under which the solvent and acidic liquid are contacted may include ambient temperature and standard pressure.

One particular embodiment of the present invention may be described with reference to FIG. 1, which shows a treatment process employing an acidic liquid of acid to treat solvent. Treatment system 10 includes solvent stream conduit 12 in fluid communication with tank 14, which may also be referred to as column 14. Conduit 12 carries solvent to be treated 11. Conduit 12 may be in fluid communication with tank 14 via inlet 16 located at or near lower end 18 of tank 14. Inlet 16 may be adapted with a diffuser 20. The diffuser may include a nozzle or simply a pipe having holes therein. An outlet 22 may be positioned at or near the upper end 24 of tank 14.

The liquid media within tank 14 may include acidic liquid 30, hydrocarbon solvent media 32, and diffused hydrocarbon solvent 34, which may include liquid bubbles or domains of hydrocarbon solvent within the acidic liquid 30. A boundary layer or surface 36 may also exist between the acidic liquid 30 and solvent media 32. Also, boundary layers or surfaces 38 may exist between the acidic liquid 30 and the diffused hydrocarbon solvent 34.

In one or more embodiments, the volume ratio of hydrocarbon solvent in contact with the acidic liquid (which exemplary ratios are provided above) is determined as a function of the diffused solvent 34 within the acidic liquid 30 without regard to the solvent media 32. Inasmuch as it is believed that advantageous treatment of the solvent is achieved at the surfaces 38 between diffused solvent 34 and acidic liquid 30, the surface area of surfaces 38 may be advantageously increased. As those skilled in the art appreciate, the surface area of surfaces 38 can be increased by forming smaller domains of diffused solvent 34. The size of diffused solvent 34 may be characterized by a cross-sectional length of the domain, which may also be referred to as a diameter, which may be more appropriate for spherical domains or those domains that are generally spherical. In one or more embodiments, the diameter of the solvent domains may be less than 12 mm, in other embodiments less than 8 mm, in other embodiments less than 5 mm, in other embodiments less than 2 mm, in other embodiments less than 1 mm, in other embodiments less than 0.5 mm, and in other embodiments less than 0.1 mm.

Inasmuch as the solvent 11 to be treated has a lower density than the acidic liquid 30, the solvent 11, in the form of diffused solvent 34, will rise through acidic liquid 30 and form solvent medium 32, which includes treated solvent. Solvent medium 32 is then removed from tank 14 via outlet 22.

As those skilled in the art appreciate, the residence time (i.e. the time that the diffused solvent 34 is in contact with acidic liquid 30, can be adjusted by using several parameters. For example, the height of liquid medium 30 within tank 14 can be adjusted to tailor the desired residence time. In one or more embodiments, where a cylindrical column is employed as tank 14, the aspect ratio (i.e. length or height to diameter) of the acidic liquid 30 may be at least 1:1, in other embodiments at least 3:1, in other embodiments at least 5:1, and in other embodiments from about 1.5:1 to about 10:1.

In one or more embodiments, solvent is continuously treated by contacting a stream of solvent with a substrate containing acidic groups and/or proton donor groups. In one or more embodiments, the solvent is passed through the substrate, which may be positioned in a manner to allow fluid flow through or past the substrate.

The proton donor groups may include any Bronsted-acid group that is capable of donating a proton to another species capable of accepting the proton (i.e. a Bronsted base). Proton donor groups may include, but are not limited to, a sulfonate group ($-OSO_3H$), phosphorate groups ($-OPO_3H_2$), perchlorate groups, and nitrate groups, as well as metalate groups such as tungstenate groups. In these or other embodiments, acidic groups include those groups that may be present in gels such as sulfated zirconia or tungstenated zirconia.

The substrate to which the proton donor groups are attached may include a variety of substrates including organic resins and inorganic gels. For purposes of simplicity within this specification, the term resin and/or gel is used interchangeably. In one or more embodiments, the resinous material is not materially affected by the solvent. For example, the solubility of the resinous material within the solvent is low or negligible. In one or more embodiments, the resinous material is insoluble within the solvent.

In one or more embodiments, the resinous material to which the proton donor groups are attached is a hydrocarbon material such as a crosslinked polystyrene resin. In these or other embodiments, the resinous material is a crosslinked divinyl benzene gel. In other embodiments, the resinous material is an inorganic gel such as silica, alumina gel, or a zirconia gel.

In one or more embodiments, the resin containing the proton donor groups is a porous solid. In these or other embodiments, the resin containing the proton donor groups is a particulate solid having an average diameter (or bead size) of less than 6 mm, in other embodiments less than 5 mm, in other embodiments less than 4 mm, and in other embodiments from about 2 mm to about 7 mm. In one or more embodiments, the resin is a porous particulate. In other embodiments, the resin is a granular material. The granular material may have an average particle size (i.e. average diameter) of from about 10 microns up to about 500 microns, in other embodiments from about 25 microns up to about 450 microns, and in other embodiments from about 35 microns to about 400 microns.

In particular embodiments, the resin containing the proton donor groups may include a sulfonated tetrafluorethylene copolymer. These resins are available under the tradename Nafion™ (Dupont). In other embodiments, the resin containing the proton donor groups may include sulfated polystyrene such as that available under the tradename Sicacide™. Other examples include sulfated zirconia and tungstated zirconia. In one or more embodiments, the resins include polymers with acid sites including crosslinked polymer resins containing acid sites.

In one or more embodiments, the residence time, which is the amount of time the solvent and resin are in contact with each, may be at least 1 minute, in other embodiments at least 3 minutes, in other embodiments at least 5 minutes, and in other embodiments at least 7 minutes. In these or other embodiments, the residence time my be less than 30 minutes, in other embodiments less than 20 minutes, in other embodiments less than 15 minutes, and in other embodiments less than 12 minutes. Those skilled in the art appreciate that the residence time within the solvent can be controlled by the flow rate of the solvent through the resinous media. Those skilled in the art also appreciated that the flow rate may be impacted by the back pressure caused by the resin within the column.

The conditions under which the solvent and resin are contacted may include a temperature of at least 0° C., in other embodiments at least 10° C., and in other embodiments at least 20° C. In these or other embodiments, the temperature may be less than 65° C., in other embodiments less 50° C., in other embodiments less than 35° C., and in other embodiments less than 30° C. The pressure may range from slight vacuum up to 6 atmospheres, in other embodiments less than 4 atmospheres, and in other embodiments less than 2 atmospheres. In one or more embodiments, the conditions under which the solvent and the resin are contacted may include ambient temperature and standard pressure.

Figure 2:
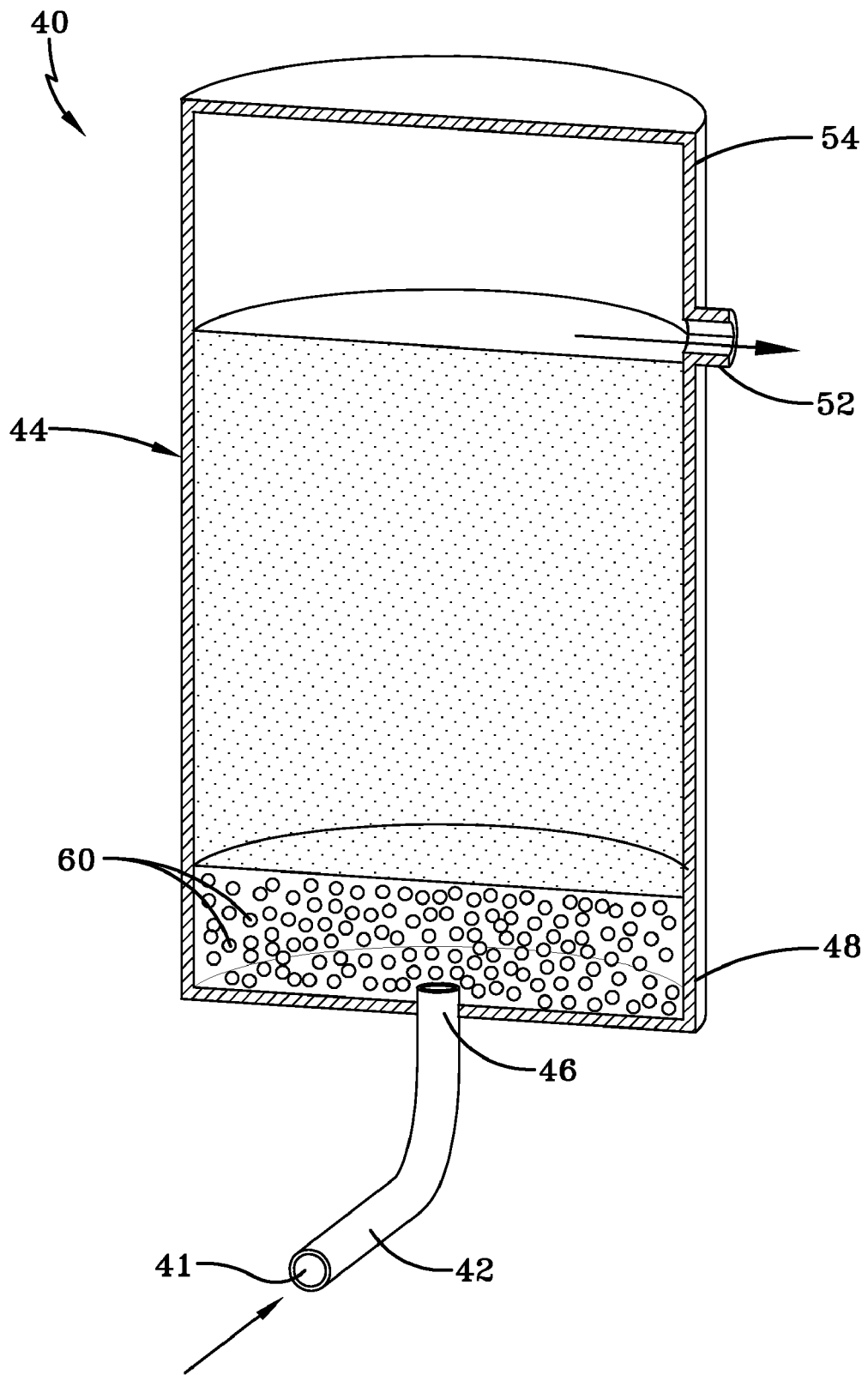
FIG. 2 is a schematic depiction of a treatment process of one embodiment of the present invention where an acidic resin is employed to treat a solvent stream.

One particular embodiment of the present invention may be described with reference to FIG. 2, which shows a treatment process employing a resin containing proton donor groups to treat solvent. Treatment system 40 includes solvent stream conduit 42 in fluid communication with resin column 44. Conduit 42 carries solvent to be treated 41. Conduit 42 may be in fluid communication with column 44 via inlet 46 located at or near lower end 48 of column 44. An outlet 52 may be positioned at or near the upper end 54 of column 44. Resin material 60, which contains proton donor groups, may be packed within column 44.

Solvent to be treated 11 entering column 44 is forced through resin material 60. Where the resin is porous, the solvent may pass through the pores of the resin. Where the resin is in the form of particulate or granular material, the solvent may pass through openings provided between the particles or granules.

In one or more embodiments, the resinous material containing the one or more proton donor groups may be placed within a packed bed, a fluidized bed, or a moving bed, as is known in the art of purification gels.

In one or more embodiments, the treatment processes of the present invention may be supplemented with additional, optional treatment steps. For example, the solvent may be optionally delivered to a neutralizing or desiccating zone where residual acid entrained within the solvent can be neutralized by a basic material such as calcium hydroxide.

In addition to or in lieu of a neutralizing or desiccating treatment process, the solvent can also be treated by distillation, adsorption, or like. For example, the adsorption may be conducted with a silica or alumina gel column followed by neutralization of the acid and desiccation with calcium hydroxide. In alternate embodiments, the treated solvent is subsequently treated by neutralization followed by adsorption treatment.

In one or more embodiments of the present invention, practice of the invention may advantageously remove or reduce catalyst residues, unreacted monomer, or other oxygenates within the solvent.

Inasmuch as the impurities, particularly oxygenates, may be deleterious to catalysts employed in the polymerization of monomer, particularly olefinic monomer, the practice of the present invention may be advantageously employed in combination with a polymerization process. In one or more embodiments, the solvent treatment process of the present invention may be employed to treat solvent raw materials purchased or obtained from suppliers. In these or other embodiments, the treatment process of the present invention may be employed to treat solvent being circulated or recycled within a polymerization process. In other words, solvent separated from polymer product may be treated according to the present invention before the solvent is introduced with new raw material such as monomer or catalyst.

In one or more embodiments, the treatment process of this invention is used in conjunction with a solution polymerization process. Solution polymerization processes are well known in the art. Exemplary systems include those employing anionic polymerization techniques. Others include those employing coordination catalyst techniques such as those using lanthanide-based, nickel-based, and cobalt-based systems.

In one or more embodiments, the treatment process of the present invention in used in conjunction or combination with a polymerization process for the manufacture of high-cis polydienes such as high-cis-1,4-polybutadiene. In particular embodiments, the polymerization process for the manufacture of high-cis-1,4-polybutadiene employs a lanthanide-based catalyst system such as neodymium-based system. These systems, and polymerization processes in which they are used, are known in the art as described in U.S. Pat. Nos. 3,297,667; 3,541,063; 3,794,604; and 4,461,883, which are incorporated herein by reference. Practice of the present invention in combination with polymerization processes that are particularly susceptible to impurities (i.e. are deleteriously impacted by) such as neodymium-based system is particularly advantageous.

In one or more embodiments, the treatment process of the present invention is used in conjunction or combination with a polymerization process for the manufacture of medium vinyl polydienes or copolymers of conjugated diene and vinyl aromatic monomer. In particular embodiments, the polymerization process employs an organolithium compound as an initiator to effect the polymerization of conjugated dienes, and optionally monomer copolymerizable therewith such as styrene. These processes are well known in the art as disclosed in U.S. Pat. Nos. 5,332,810, 5,329,005, 5,578,542, 5,393,721, 5,698,646, 5,491,230, 5,521,309, 5,496,940, 5,574,109, and 5,786,441, which are incorporated herein by reference.

Various modifications and alterations that do not depart from the scope and spirit of this invention will become apparent to those skilled in the art. This invention is not to be duly limited to the illustrative embodiments set forth herein.

The invention claimed is:

1. A method for treating a hydrocarbon solvent, the method comprising:
continuously introducing a hydrocarbon solvent to a medium including sulfated zirconia, tungstenated zirconia, or both sulfated zirconia and tungstenated zirconia, where the hydrocarbon solvent is contaminated with oxygenates;
allowing the hydrocarbon solvent to be in contact with the medium for at least 1 minute;
continuously removing hydrocarbon solvent from the medium to provide a treated hydrocarbon solvent stream;
further comprising the step of employing at least a portion of the treated hydrocarbon stream as a solvent within a polymerization process; and
circulating the solvent from the polymerization process back to the medium containing one or more proton donor groups.

2. The method of claim 1, where the polymerization process includes the polymerization of olefins.

3. The method of claim 1, where the polymerization process employs a lanthanide-based catalyst system.

4. The method of claim 1, where the hydrocarbon solvent is selected from the group consisting of n-pentane, iso-pentane, n-hexane, methyl pentane, n-heptane, methyl hexane, ethyl pentane, n-octane, 2-ethyl hexane, n-nonane, and n-decane.

5. The method of claim 1, where said contact time is at least 3 minutes at a temperature of at least 10° C.

6. The method of claim 5 where said step of allowing the hydrocarbon solvent to be in contact takes place at less than 4 atmospheres.

7. The method of claim 1, where the polymerization process includes the polymerization of conjugated diene monomer.

8. The method of claim 7, where the polymerization process further includes the polymerization of vinyl aromatic monomer.

9. A method for treating hydrocarbon solvent, the method comprising:
contacting a hydrocarbon solvent contaminated with oxygenates with a medium including sulfated zirconia, tungstenated zirconia, or both sulfated zirconia and tungstenated zirconia and recovering a solvent having reduced oxygenate contamination.

10. The method of claim 9, where the hydrocarbon solvent is selected from the group consisting of n-pentane, iso-pentane, n-hexane, methyl pentane, n-heptane, methyl hexane, ethyl pentane, n-octane, 2-ethyl hexane, n-nonane, and n-decane.

11. The method of claim 10, where said step of contacting takes place at a temperature of at least 10° C. for at least 3 minutes.

12. The method of claim 11, where said step of contacting takes place at less than 4 atmospheres.

13. A method for treating hydrocarbon solvent, the method comprising the steps of:
(i) providing a hydrocarbon solvent contaminated with oxygenates;
(ii) treating the hydrocarbon solvent by passing the solvent through a column containing alumina, silica, or both alumina and silica;
(iii) treating the hydrocarbon solvent by passing the solvent through a column containing a solid substrate containing proton donor groups; and
(iv) employing at least a portion of the treated hydrocarbon solvent within a polymerization process.

14. The method of claim 13, further comprising the step of treating the hydrocarbon solvent by distillation.

15. The method of claim 14, where the hydrocarbon solvent is selected from the group consisting of n-pentane, iso-pentane, n-hexane, methyl pentane, n-heptane, methyl hexane, ethyl pentane, n-octane, 2-ethyl hexane, n-nonane, and n-decane.

16. The method of claim 15, further comprising the step of using the solvent in a second polymerization process, where the first polymerization process includes anionic polymerization and where the second polymerization process includes coordination catalysis employing a lanthanide-based catalyst system, and where said step of (ii) treating and said step of (iii) treating take place between said first polymerization process and said second polymerization process.

17. The method of claim 16, where the first polymerization process includes the anionic polymerization of conjugated diene monomer and optionally monomer copolymerizable therewith, and where the second polymerization process includes the coordination catalysis of conjugated dienes to form high-cis polydienes.

18. The method of claim 13, where the solid substrate containing proton donor groups is a sulfated zirconia, tungstenated zirconia, or both sulfated zirconia and tungstenated zirconia.

* * * * *